United States Patent [19]

Barberet et al.

[11] Patent Number: Plant 5,420

[45] Date of Patent: Mar. 19, 1985

[54] CARNATION NAMED LONBELIT

[75] Inventors: Nicole Barberet; Yves Ducloux, both of Antibes, France

[73] Assignee: Laboratoire de Physiologie Vegetale de La Londe, Antibes, France

[21] Appl. No.: 512,474

[22] Filed: Jul. 11, 1983

[51] Int. Cl.[3] ..... A01H 5/00

[52] U.S. Cl. ..... Plt./72

[58] Field of Search ..... Plt./72

*Primary Examiner*—Robert E. Bagwill

*Attorney, Agent, or Firm*—Charles W. Rummler

[57] ABSTRACT

A new carnation cultivar distinguished by the Crimson and Neyron Rose coloration of its medium sized blooms, the petals of which are very numerous and quite densely packed to present a ball of almost solid color. This new plant is also characterized by its recurrent habit of blooming profusely in the midseason of Spring and Fall to provide flowers with long, strong stems and long lasting quality for vase keeping. This new plant also has a vigorous and strong growth habit which enhances its practicability for greenhouse culture for cut flower production.

1 Drawing Figure

BACKGROUND OF THE NEW PLANT

This new carnation plant originated as a seedling from our crossing of varieties selected from breeding stock, maintained at La Londe, Les Maures, France, in the course of breeding efforts carried on by us since 1978 with the object of producing new varieties having better color and good growth characteristics, as well as to create varieties resistant to Fusarium Oxysporum which so often makes carnation culture quite difficult. We selected this plant from a group of the seedlings resulting from the aforesaid crossing because of the beauty of its flowers borne on long, straight and upright stems and we propagated it at La Londe, by means of cuttings from the discovery plant to test its capability of retaining its distinctive characteristics. Propagation of this new plant was carried on under our direction through several successive generations and it was thus determined that the distinctive characteristics of the new variety held true from generation to generation and appeared to be firmly fixed.

DESCRIPTION OF THE DRAWING

Our new carnation cultivar is illustrated by the accompanying photographic drawing which shows, in full color, an arrangement of buds, partially opened flowers and full blooms, the colors shown being as nearly true to those specified herein as it is reasonably possible to obtain by conventional photograhic procedures.

DESCRIPTION OF THE NEW PLANT

The following is a detailed description of our new carnation plant based upon observations of greenhouse grown plants made at La Londe, France, in the Spring of 1983, and the color designations are according to The R.H.S. Colour Chart published by The Royal Horticultural Society of London, England.

THE PLANT

Origin: Seedling.

Parentage:

*Seed parent.*—Breeding Stock Plant No. 393 C (unpatented).

*Pollen parent.*—Breeding Stock Plant No. 74 C 21 (unpatented). These are unnamed varieties individually identified in our permanent records and maintained for breeding purposes in our collection of carnation plants at La Londe, France.

Classification:

*Botanic.*—Hybrid *Dianthus caryophyllus.*

*Commercial.*—Standard Carnation.

Form: Tall bush.

Height: About 107 cm. at eight months.

Main stem length: Less than 15 cm. due to pinching.

Branching character: At least four stems emitted near the ground.

Growth: Vigorous, upright and very strong.

Foliage:

*Quantity.*—Not very abundant.

*Number of leaves.*—More than 120.

*Size of leaf.*—Average; at the 7th node, about 10 cm. long and about 1.1 cm. wide.

*Leaf shape.*—Linear with rolled margins.

*Texture.*—Leathery.

*Color.*—Upper side — 189A and 189B. Under side — 189A and 189B. (The colors stated are to include nuances and are as close as can reasonably be averaged from the specimens observed.)

*Ribs and veins.*—Hardly noticeable.

THE BUD

Size: Medium. Diameter — About 2.1 cm. Length — About 3 cm.

Form: Ovoid.

Rate of opening: Normal.

Color of petals: When sepals first divide and when petals begin to unfurl, the colors are the same as when the flower is in full bloom.

Sepals:

*Number.*—Five.

*Shape.*—Generally ovate in the upper portion and joined together at the lower part, the apex being sharply pointed. The sepals are hooded over the bud and stand up when the flowers open.

*Color.*—Inside — Greenish White. Outside — 138B and 145A.

*Striae.*—The striae are longitudinal.

Calyx:

*Shape.*—Bell shaped.
*Size.*—Medium.
*Splitting.*—The calyx very rarely splits.
Aspect.—Smooth.

Flower stem:
*Length.*—About 73 cm.
*Character.*—Erect and rigid.
*Color.*—189A and 189B.

THE FLOWER

Blooming habit: Recurrent and profusely, blooming in the midseason of Spring and Fall.

Size: Medium. Average diameter — About 8.7 cm. Average depth — about 5.7 cm.

Borne: Singly.

Shape:
*When bloom first opens.*—High centered.
*When bloom matures.*—Dome-shaped.

Petalage:
*Number of petals.*—About 72 to 93, averaging about 83.
*Arrangement.*—Imbricated.
*Form.*—Almost circular with serrated tips.
*Texture.*—Soft.
*Appearance.*—Satiny.
*Color.*—Outer and Inside Petals: Body — 52A and 55A. Base — Greenish White. Reverse side — 55A and 55C.

Petaloids:
*Number.*—From 5 to about 12.
*Size.*—Smaller than petals.

*Color.*—The same as the petals.

Flower stem:
*Length.*—About 73 cm. (cut at tenth node).
*Character.*—Strong and upright.
*Color.*—189A and 189B.

Fragrance: Present in general.

Persistence: Flowers hang on and dry.

Lasting quality: As cut flower in vase keeping — At least ten days.

REPRODUCTIVE ORGANS

Stamens:
*Number.*—10 To 18 arranged around the pistils.
*Anthers.*—Size: Less than 4 mm. Color: Whitish.
Filaments.—Color — Whitish.

Pistils:
*Number.*—Three (exceptionally four).
*Styles.*—Color — Pink.
*Stigmas.*—Color — Pale Pink.

Character of ovaries: The ovary is ribbed.

The distinctive character of this new carnation variety resides in the Crimson and Neyron Rose color of its flowers and the large number of petals in each flower which presents a very beautiful and solid looking color mass.

We claim:

1. The new and distinct hybrid carnation, substantially as herein shown and described, characterized by the unique form and color of its blooms and its profuse production of flowers during its blooming periods.

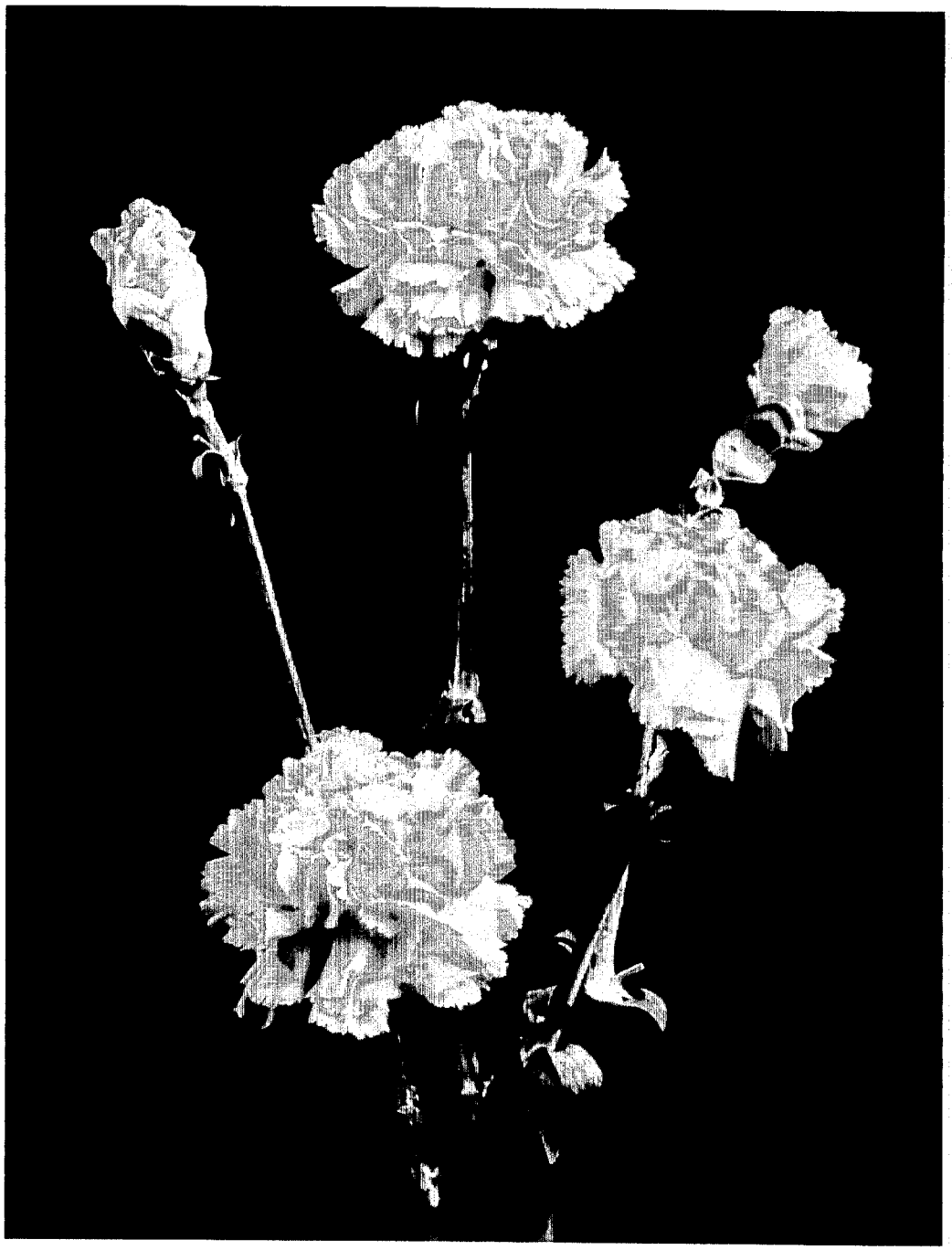

* * * * *